United States Patent [19]

Howard

[11] Patent Number: 5,060,661
[45] Date of Patent: Oct. 29, 1991

[54] INFLATABLE NECK AND HEAD SUPPORT

[76] Inventor: Thomas L. Howard, 1972 Scudder Dr., Akron, Ohio 44320

[21] Appl. No.: 535,127

[22] Filed: Jun. 8, 1990

[51] Int. Cl.5 ............................................. A61F 5/00
[52] U.S. Cl. .................................. 128/845; 128/89 R; 128/869; 128/87 R; 128/DIG. 23; 441/113
[58] Field of Search ............. 128/845, 857, 869, 76 R, 128/87 B, 87 R, DIG. 20, DIG. 23; 5/441; 137/223; 441/123, 108, 113, 81

[56] References Cited

U.S. PATENT DOCUMENTS

| | | | |
|---|---|---|---|
| 1,341,272 | 5/1920 | Jordahn | 441/113 |
| 3,048,860 | 8/1962 | Richardson | 128/DIG. 23 X |
| 3,765,412 | 10/1973 | Ommaya et al. | 128/857 X |
| 4,617,691 | 10/1986 | Monti et al. | 128/DIG. 23 X |
| 4,657,003 | 4/1987 | Wirtz | 128/869 |
| 4,676,233 | 6/1987 | Scheinberg | 128/87 R |

*Primary Examiner*—Robert A. Hafer
*Assistant Examiner*—Kerry Owens
*Attorney, Agent, or Firm*—Joseph Januszkiewicz

[57] ABSTRACT

An inflatable neck and head support for use by a wearer which is a generally rectangular body of flexible gas impervious material with two side panels that is sealed around its entire periphery to form a closed chamber. A valve is mounted in such body to inflate and deflate the chamber. Fastening means are mounted on spaced portions of the body to permit securing the rectangular shape into an annular shape to encompass the neck and support the head of a wearer.

4 Claims, 3 Drawing Sheets

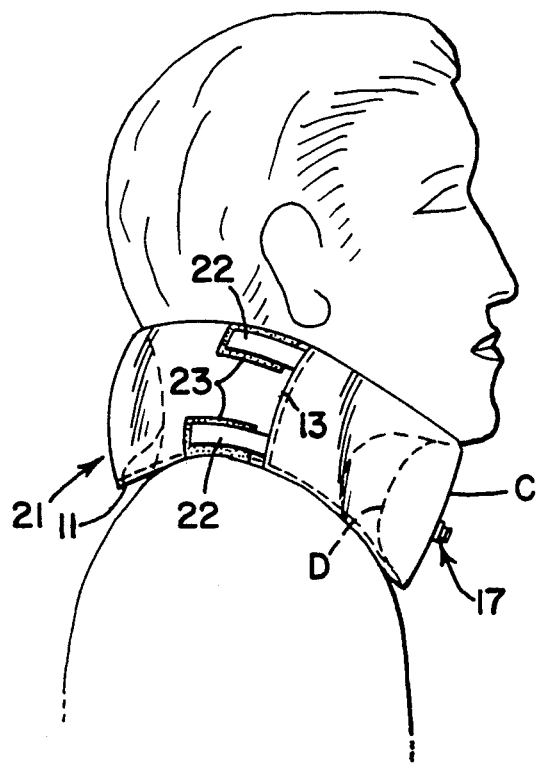
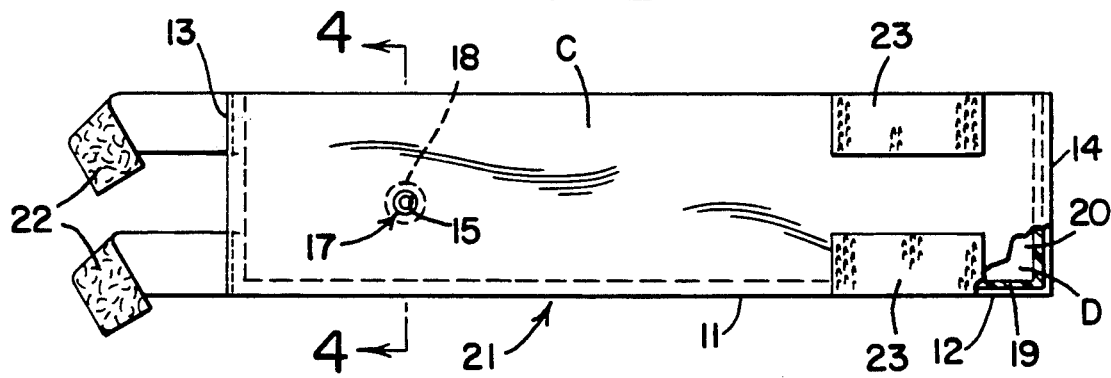
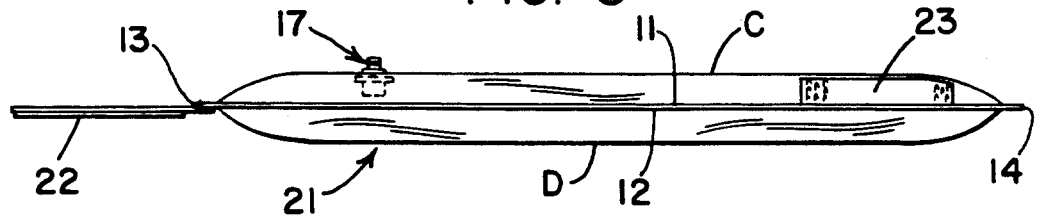

INFLATABLE NECK AND HEAD SUPPORT

BACKGROUND OF THE INVENTION

This invention relates to an inflatable neck support which supports the head in its natural position of elevation for stability without interfering with its normal use and to the method of making such inflatable support. Upon inflation of such neck and head support, such support is extremely useful as an aid in supporting the head of a handicapped wearer who is using a life preserver in water assuring proper attitude to eliminate the taking on of water. Such neck support gives the wearer a good posture for better body control in the water.

Where a handicapped person wears a life preserver, it is important that another individual give that person full attention at all times, as the handicapped person has limited mobility and can be quickly put into a dangerous condition of drowning by a momentary inattention from the accompanying attendant, which will thereafter place the handicapped person in fear of any subsequent water immersion conditions. With the neck support, the handicapped person can be assured of a controlled condition for going into the water without fear of swallowing water or being put into position of danger in water as the support stabilizes the head and provides a controlled environment. In emergency situations the inflatable neck and head support can be used to support the head of an injured individual by transferring the support away from the neck and onto the shoulders to stabilize the head and neck. Of particular interest is that the chamber can be inflated to where the collar or neck support is comfortable to the wearer and there is no need to fully inflate to a given pressure. By so inflating the neck support, the annular shape will adjust to the contour of wearer's neck.

SUMMARY OF THE INVENTION

An inflatable neck and head support for use by a wearer which has a generally rectangular shape and made from a flexible gas impervious material preferably that is heat sealable. The rectangular body is sealed around its entire periphery to define a closed chamber that is inflatable and deflatable via a valve mounted in said body. Fastener means such as bristle hook and loop material is mounted on spaced portions of the body to allow upon inflation of the chamber to form an annular shape and retain such annular shape. A modification of such support has a thin layer of closed cell foam adhered to a wall of the closed chamber to provide a degree of rigidity to the head support.

BRIEF DESCRIPTION OF THE DRAWINGS

FIG. 1 is a side elevational view of an inflated neck and head support of a preferred embodiment of the invention in place about the neck of a wearer;

FIG. 2 is a side elevational view of the neck and head support in a deflated condition with a portion thereof in section;

FIG. 3 is a plan view of the neck and head support;

DESCRIPTION OF THE PREFERRED EMBODIMENT

Figure 4:
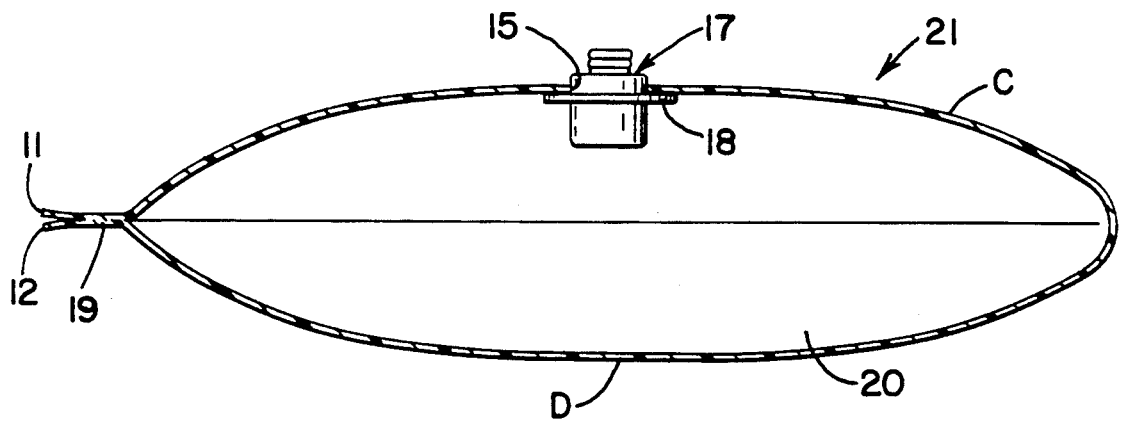
FIG. 4 is a cross section of the neck and head support taken on line 4—4 of FIG. 2.
Figure 5:
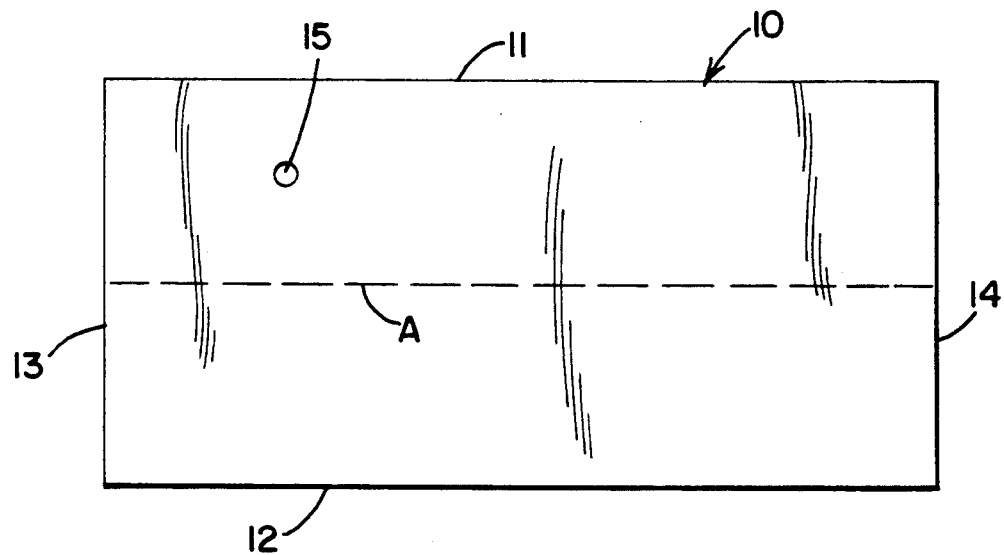
FIG. 5 is a side elevational view of a rectangular piece of elastomeric material showing the neck and head support prior to assembly.

Referring to the drawings, wherein like reference numerals designate like or corresponding parts throughout the several views, there is shown in FIG. 5 a rectangular piece of flexible gas impervious material 10 such as a heat sealable polyurethane coated nylon with an upper side edge 11, a lower side edge 12, and two end edges 13 and 14. A hole 15 is punched out of the material 10 in the upper left quadrant as viewed in FIG. 5. A suitable valve 17 is installed onto such gas impervious material 10 with a portion thereof extending outwardly through the hole 15. Such valve 17 has an annular flange 18 to facilitate its mounting onto the material 10 and to reinforce the annular area around the hole 15. Such valve 17 can be used to easily inflate and deflate the chamber area to be described that is to be formed by the gas impervious material 10. The length of the tubular portion of valve 17 that projects outwardly away from the valve body can be of any desired length to either facilitate the wearer to be able to reach such valve 17 to inflate it himself or to have a shorter length for others to so inflate. For purposes of illustration, a short valve length is shown. Such valve 17 is manufactured by the Halkey Roberts Corporation of Paramus, New Jersey and is illustrated by U.S. Pat. No. 2,859,932. The rectangular piece of gas impervious material 10 is folded over along a center line A designated in FIG. 5 to form a flat strip. The respective end edges 13 and 14 are folded over onto themselves while the upper edge 11 is folded onto lower edge 12, which edges are then heat sealed as at 19 (FIG. 2) to form a closed chamber 20 which can be inflated and deflated via valve 17 (FIG. 4). The heat sealing of such edges forms an elongated or longitudinally extending flat inflatable neck and head support 21 which in effect has a pair of side panels designated C and D in FIG. 4 that are thus sealed around their entire periphery presenting a pair of spaced side edges and a pair of spaced end edges which defines such chamber 20.

To facilitate the use of such neck and head support 21, a pair of elongated strips of VELCRO ® fastener material 22 have their one edges adhered to the one edge of neck support 21, and another pair of flat strips of VELCRO ® material 23 suitably adhered to the other end body portion of neck support 21. VELCRO ® fastener material is a face-to-face, bristle hook and loop type material, which when placed into engagement provides a ready means to adjustably secure the neck and head support in a given position. Other suitable adjustable fastener means may be used in lieu of the flat bristle hook and loop type material such as buckle and straps. With the use of a pair of fastener strips, there is provided a degree of stiffness and firmness to the neck support to provide stability in the vertical direction for the head of a wearer of the support.

In lieu of using a single rectangular piece of flexible gas impervious material 10 two single pieces or panels of flexible gas impervious material similar to panels C and D may be used, wherein the two rectangular panels are of the same size and are placed in abutting contact with their respective sides being coincident with each other. As in the first embodiment, such material is preferred to be of a heat sealable material. A hole is punched out in one of the panels and an inflation valve is then installed to such hole. The entire periphery of the two panels are then heat sealed together to form a rectangular shaped elongated body with a closed chamber. Fastening means are then secured to the respective ends of the rectangular shaped body so that upon encircling the wearer's neck and inflating such chamber, the rectangular body assumes an annular inflated shape for supporting the neck of a wearer.

In the use of such inflatable neck and head support, the uninflated support is wrapped loosely around the neck of a wearer. The strips of fastener material 22 is positioned onto the companion fastener flat strips 23 to secure the support 21 onto the wearer's neck through the face-to-face bristle hook and loop type fastener material. Thereafter air is forced into the closed chamber 20 to slowly inflate such chamber 20 such that the annular shape of the support 21 will adjust to the contour of the wearer's neck, head and adjacent shoulders. The annular shape behind the neck abuts the neck portion, as do the respective sides. The forward portion has sufficient clearance to support a portion of the wearer's chin, thus providing support for the head in its natural position of elevation with stability.

Figure 6:
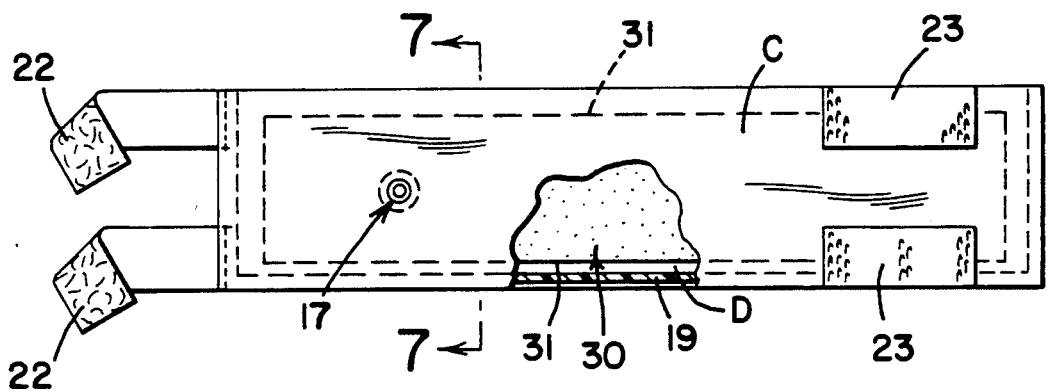
FIG. 6 is a side elevational view of a modified construction of the neck and head support in a deflated condition.
Figure 7:
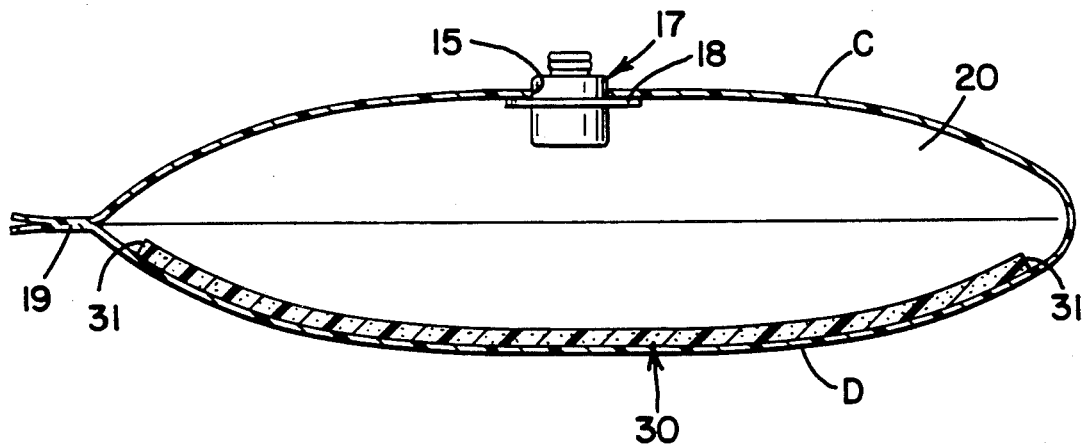
FIG. 7 is a cross-sectional view of the modified construction of the neck and head support taken on line 7—7 of FIG. 6.

A modification of the described neck and head support is shown in FIGS. 6 and 7 wherein the support is identical to that shown in FIGS. 2, 3 and 4 except that an elongated thin sheet of closed cell foam 30 with edges 31 is suitably adhered to panel D. Since the structures are identical, the same reference numerals will be used with the addition of numerals 30 and 31 to identify the sheet of closed cell foam and the edges 31. Such sheet of closed cell foam 30 has its width and length substantially the same dimensions as panel D with sufficient clearance to allow for the ease of heat sealing the edges of the rectangular piece of gas impervious material of which such neck and head support is made.

As in the first embodiment, a hole is punched out of the material with a valve installed thereon to facilitate the inflation and deflation of the closed chamber 20 once the heat sealing as at 19 of the peripheral edges is achieved. The thin sheet of closed cell foam provides sufficient stiffness to the support to assure the wearer that his head will maintain a vertical attitude to his body when in a vertical position. Thin as used above in reference to the thickness of a thin sheet of closed cell foam is to define over the word film which is considered to be of extreme thinness.

Figure 8:
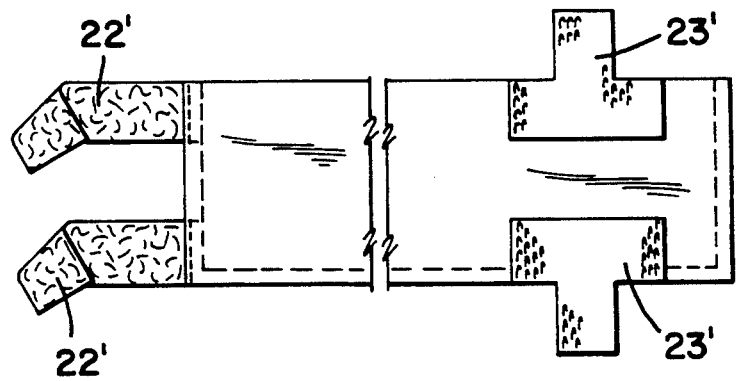
FIG. 8 is a fragmentary side elevational view of a neck and head support as shown in FIG. 2 but with a modified fastening means.

A further variation on the above described embodiments is to have the face-to-face bristle hook and loop type material configured as shown in FIG. 8. The fastener material is the same as that described with respect to the prior embodiments wherein strips 22' that are attached to one free end of the neck and head support has the hook material on both free surfaces. The cooperative fastener strips 23' that are mounter on the other side of the neck support are T-shaped and are fastened to the support with lateral portions extending away from the support so that when the fastener strips 22' are placed onto strips 23', the support is secured in place. Then the lateral free extending portions of strip 23' are folded over onto the exposed portion of strip 22' to double lock the fasteners 22' and 23' together.

While certain representative embodiments and details have been shown and described for the purpose of illustrating the invention, it will be apparent to those skilled in the art that various changes and modifications other than those referred to may be made therein without departing from the spirit or scope of the invention.

What is claimed is:

1. A personal floatation support for use around the neck of a wearer for supporting the head of a wearer in water consisting of a substantially rectangular body of flexible gas impervious material, said rectangular body having a pair of overlapping side panels, said side panels having a pair of spaced side edges and a pair of spaced end edges that are sealed to form a closed inflatable chamber, fastener means mounted adjacent to said end edges on said body for securing said flexible rectangular body into an annular shape for encompassing the neck of a wearer upon inflation, and valve means mounted on said rectangular body for connection to said chamber for providing pressurized gas to said chamber to convert said rectangular body from a collapsed flexible condition to an inflated annular flexible shape that holds the head in an upright position while permitting free movement in a side to side position wherein said fastener means includes strap means having one end secured to one of said end edges of said support, said strap means having two opposed faces of hook material, and T-shaped strips secured to the rectangular body adjacent the remaining one of said end edges of said support, each of said T-shaped strips having a head portion and a stem portion, said stem portion being a short perpendicular portion extending from said head portion and away from said rectangular body portion, said head portion being secured to said body, and said T-shaped strips having loop material faces thereon for cooperative locking action with said strips, and the free end portion of said stem secured over said strap means when said strap means is secured to said head portion of said T-shaped strips to provide a double locking.

2. A personal inflatable floatation support as set forth in claim 1 wherein said fastener means are plural means to provide body to said support thereby stabilizing the neck of a wearer.

3. A personal inflatable floatation support as set forth in claim 1 wherein said fastener means comprises at least a pair of laterally spaced fastener means to provide stiffness to said support in a direction parallel to said end edges along the full length of said support when formed into said annular shape.

4. A personal inflatable floatation support as set forth in claim 1 wherein one of said side panels has a closed cell foam sheet secured thereto along its length and width to provide body and sufficient rigidity in said annular shape to stabilize the head of a wearer of said support.

* * * * *